US010925265B2

(12) United States Patent
Heetjans

(10) Patent No.: US 10,925,265 B2
(45) Date of Patent: Feb. 23, 2021

(54) DEVICE, SYSTEM AND METHOD FOR RESIDUE USE IN LIVESTOCK FARMING

(71) Applicant: BIG DUTCHMAN INTERNATIONAL GMBH, Vechta (DE)

(72) Inventor: Kai Heetjans, Hoogstede (DE)

(73) Assignee: BIG DUTCHMAN INTERNATIONAL GmbH, Vechta (DE)

( * ) Notice: Subject to any disclaimer, the term of this patent is extended or adjusted under 35 U.S.C. 154(b) by 295 days.

(21) Appl. No.: 16/040,079

(22) Filed: Jul. 19, 2018

(65) Prior Publication Data

US 2019/0021296 A1    Jan. 24, 2019

(30) Foreign Application Priority Data

Jul. 21, 2017    (DE) .......................... 202017104380.0

(51) Int. Cl.
| | |
|---|---|
| *A01K 67/033* | (2006.01) |
| *A01K 1/01* | (2006.01) |
| *C05F 17/05* | (2020.01) |
| *C05F 17/80* | (2020.01) |
| *A01K 29/00* | (2006.01) |
| *C05F 3/06* | (2006.01) |

(52) U.S. Cl.
CPC .......... *A01K 67/033* (2013.01); *A01K 1/0135* (2013.01); *A01K 29/00* (2013.01); *C05F 3/06* (2013.01); *C05F 17/05* (2020.01); *C05F 17/80* (2020.01)

(58) Field of Classification Search
CPC .... A01K 67/033; A01K 1/0135; A01K 29/00; A01K 63/04; C05F 17/05; C05F 17/80
USPC .......................... 119/6.6, 6.5, 232, 236, 442
See application file for complete search history.

(56) References Cited

U.S. PATENT DOCUMENTS

| | | | | |
|---|---|---|---|---|
| 4,040,810 | A * | 8/1977 | Eby .......................... | C05F 3/00 71/9 |
| 4,262,633 | A | 4/1981 | Taboga | |
| 6,001,146 | A * | 12/1999 | Olivier .................... | C05F 17/05 71/9 |
| 9,353,018 | B2 * | 5/2016 | Kitazumi ................. | C05F 3/06 |
| 2015/0223496 | A1 * | 8/2015 | Kitazumi ................. | B09B 5/00 119/6.5 |
| 2020/0281176 | A1 * | 9/2020 | Whitaker ............. | A01K 67/033 |

FOREIGN PATENT DOCUMENTS

| | | |
|---|---|---|
| EP | 2 703 372 A1 | 3/2014 |
| EP | 2703372 | 3/2014 |
| RU | 2 285 400 C2 | 4/2006 |
| RU | 2285400 | 4/2006 |
| WO | 0132586 | 5/2001 |

(Continued)

*Primary Examiner* — Yvonne R Abbott-Lewis
(74) *Attorney, Agent, or Firm* — Price Heneveld LLP

(57) ABSTRACT

A device, system, and method for residue use in livestock farming, comprising a conveyor device for conveying animal excrement along a conveyor section, wherein the conveyor section has a larva-introducing portion for metering in larvae and/or larva eggs, an excrement-introducing portion for metering in animal excrement depending on one or more process parameters, and a larva-separating portion for separating the larvae, and methods for use thereof.

15 Claims, 11 Drawing Sheets

(56) References Cited

FOREIGN PATENT DOCUMENTS

| WO | 2002011531 | 2/2002 |
| WO | 2007059537 | 5/2007 |
| WO | 2007059537 A1 | 5/2007 |
| WO | 2008134865 | 11/2008 |
| WO | 2012115959 | 8/2012 |
| WO | 2015115959 A2 | 8/2012 |

* cited by examiner

DEVICE, SYSTEM AND METHOD FOR RESIDUE USE IN LIVESTOCK FARMING

CROSS-REFERENCE TO FOREIGN PRIORITY APPLICATION

The present application claims the benefit under 35 U.S.C. § 119(b) of German Application No. DE 202017104380.0 dated Jul. 21, 2017, titled "Device, System and Method for Residue Use in Livestock Farming."

FIELD OF THE INVENTION

The invention relates to a device, a system, and a method for residue use in livestock farming.

BACKGROUND OF THE INVENTION

Residue use, in particular, the use of animal excrement, in livestock farming constitutes a challenge, in particular, with regard to costs and the reduction in emissions and pollutants. From WO 2012/115959 A2, WO 2007/059537 A1, RU 2 285 400 C2 and EP 2 703 372 A1, it is known to use larvae in residue use in livestock farming. However, existing solutions have not become widespread in practice. Existing solutions have not proven successful, in particular, due to a lack of process reliability, in particular, for livestock farming on a large scale in mass stalls.

It is, therefore, an object of the present invention to provide a device, a system, and a method for residue use in livestock farming, which improve one or more of the disadvantages mentioned, and/or to provide an improved device, an improved system and an improved method for residue use in livestock farming.

SUMMARY OF THE INVENTION

This object is achieved by a device for residue use in livestock farming, comprising a conveyor device for conveying animal excrement along a conveyor section, wherein the conveyor section has a larva-introducing portion for metering in larvae and/or larva eggs, an excrement-introducing portion for metering in animal excrement depending on one or more process parameters, and a larva-separating portion for separating the larvae.

The invention is based, inter alia, on the finding that a particularly advantageous solution can be achieved if the animal excrement is conveyed by a conveyor device along a conveyor section. It is preferred for said conveying of the animal excrement to take place while the animal excrement is being mixed with larvae and/or larva eggs and for these to live on the animal excrement, to grow therein, and to thereby reduce the quantity of animal excrement. It is, therefore, likewise particularly advantageous that the device for residue use in livestock farming has an excrement-introducing portion via which additional animal excrement can be metered in onto the conveyor device. The growth of larvae is dependent, inter alia, on the availability of sufficient food for the larvae and/or larva eggs, in particular, in the form of animal excrement, and, in particular, in a sufficient quantity and quality. For example, depending on the length of the conveyor section and/or the quantity and/or quality of the excrement introduced at the beginning and/or on the quantity and/or type of introduced larvae and/or larva eggs, different quantities of animal excrement have to be metered in in the excrement-introducing portion in order to permit as good a growth of larvae as possible.

Animal excrement can preferably also be referred to as a substrate and can be mixed, in particular, with additional substances, for example nutrients.

The metering in of larvae and/or larva eggs preferably also takes place depending on one or more process parameters, such as length of the conveyor section, the quantity and/or quality of the excrement introduced at the beginning, and the quantity and/or type of animal excrement to be metered in.

The metering in of young larvae, in particular, of approximately four days old, is particularly preferred. The young larvae are preferably produced from larva eggs, in particular, for approximately four to seven days. During this phase, the larva hatching and, preferably, feeding take place, for example with the "Gainesville diet" or equivalent "easily digestible" substrate. The metering in of young larvae has advantages over the metering in of larva eggs since the direct metering in of eggs may lead to poor hatching and poor survival of young larvae. The device for residue use in livestock farming preferably comprises a larva breeding installation in which the young larvae can be produced from larva eggs, as described here.

In the larva-separating portion, the larvae are separated; in particular, the larvae are detached from the residual excrement, in particular, from that portion of the animal excrement which has not been consumed by the larvae. When the larvae are used further, a larva harvest is frequently also discussed in this connection. The larva-separating portion is, therefore, also referred to as a harvesting portion.

The conveyor device is preferably designed as a belt conveyor and/or preferably comprises one or more belt conveyors. Such a belt conveyor preferably has a conveyor belt, which can also be referred to as a breeding belt, and is preferably designed with an endless belt having a carrying run and a return run, wherein the animal excrement is preferably conveyed on the carrying run. The conveyor device is preferably driven electrically. The conveyor device can be entirely or partially arranged in an excrement-drying device or can entirely or partially form such an excrement-drying device. An excrement-drying device is preferably of multi-stage design and generally comprises two or more partial conveyor sections one above another, which as a rule have opposed conveyor directions and are preferably formed by a plurality of belt conveyors arranged one above another. Excrement-drying devices are as a rule ventilated in order to permit good and rapid drying of the excrement.

A development of the conveyor device can also be designed as a plate conveyor and can comprise a plurality of plates which are preferably perforated in the manner of a sieve. Such a plate conveyor is preferably configured as an endless conveyor, wherein the individual plates are furthermore preferably driven by a drive, in particular, a chain drive. The plates are preferably fastened to the chain drive on at least one longitudinal side. The fastening can be configured rotatably such that the plates are connected to the chain drive in an articulated manner. The chain drive is preferably driven electrically.

It is preferred for the conveyor device to be ventilated, to be configured so as to be able to be ventilated, to have a ventilation device, and/or to be connectable to a ventilation device.

The conveyor device, in particular, a conveyor belt of the conveyor device, preferably has a perforation. The perforation is preferably smaller than 2 mm in diameter, and, therefore, the larva heads or larva bodies cannot remain stuck therein during transport and growth. Furthermore, preferably, the conveyor device, in particular, a conveyor belt of the conveyor device, is of closed design.

The device for residue use in livestock farming is preferably designed to leave young larvae in the animal excrement up to the pre-pupa stage, in particular, approximately up to an age of thirteen to fifteen days.

In a preferred embodiment, the device comprises a separating device with a larva-collecting container and/or a residual-excrement-collecting container. A preferred development is distinguished in that the separating device has a light source, a larva bridge, and/or a mechanical detaching device.

It is furthermore preferred for the light source to be arranged and/or designed to illuminate the larva-separating portion of the conveyor section. The light source is preferably arranged parallel to the direction of longitudinal extent of the larva-separating portion.

The larva bridge is preferably designed as a device via which larvae can pass from the conveyor section into the larva-collecting container, preferably by means of their own movement. The larva bridge can also be referred to as a harvesting ramp.

The larva bridge is preferably designed in such a manner that it has a slope in the direction of the conveyor device, in particular, in the direction of the conveyor belt.

Furthermore, preferably, the larva bridge has a lowering mechanism with which an end of the larva bridge that faces the conveyor device, in particular, the conveyor belt, can be lowered in the direction of the conveyor device, in particular, of the conveyor belt.

It is furthermore preferred for one or more edges of the larva bridge, in particular, the edges which are to be passed by larvae or pre-pupae, to be rounded.

Furthermore, preferably, the device for residue use in livestock farming has a pre-pupae transport belt, which can also be referred to as a larva-collecting belt, onto which the larvae or pre-pupae can pass after leaving the larva bridge and/or the larva-collecting container and on which they can be transported further.

The larva-collecting belt is preferably an endless conveyor belt composed of a textured material, for example, produced from a woven fabric, and even more preferably produced from polypropylene.

The texturing enables the pre-pupae to find a good grip and undesired blockages or accumulations do not occur. A further advantage is the lack of polarity of the material, as a result of which simple cleaning by means of a brush is possible.

The larva-collecting belt is preferably arranged in a larva channel. The larva channel is preferably designed in cross section as a U-shaped profile, wherein the opening of the U-shaped profile is preferably directed upwards and furthermore preferably with additional bevelling at the limb ends; at the upper end, said bevelling being directed inwards.

According to a preferred embodiment, the larva bridge and/or the larva-collecting container, in particular, an interior of the larva-collecting container, are arranged in such a manner that they are protected from light of the light source of the separating device. In particular, it is preferred for the larva bridge and/or the larva-collecting container, in particular, the interior of the larva-collecting container, to be arranged in such a manner that they are not illuminated by the light source of the separating device and/or are protected from light, in particular, emanating from the light source of the separating device, and/or are darkened and/or are arranged in a darkened region. It is preferred for the larva bridge and/or the larva-collecting container, in particular, the interior of the larva-collecting container, to be arranged in such a manner that they receive less light and/or can receive less light than the conveyor device in the region of the larva-separating portion.

In an alternative refinement, it is provided that the light source is arranged and/or designed, in particular, to illuminate the larva bridge and/or to substantially exclude the conveyor device in the larva-separating portion from the illumination.

It has been found that the larvae, as soon as they have developed into pre-pupae, have a sense for light. The effect specifically occurs in that the pre-pupae feel attracted to light. The light source is preferably intended to be designed to output a light colour similar to daylight, preferably white light, cold-white light, optionally with blue, UV components, and/or IR radiation. In the harvesting portion, an illumination is preferably provided outside the conveyor device, in particular, outside a conveyor belt, in particular, positioned parallel to the direction of longitudinal extent of the harvesting portion and/or in such a manner that the greatest light intensity lies outside the conveyor belt. The effect achieved by this is that the pre-pupae strive towards the light. In this refinement, the larvae are not driven out of the substrate by illumination of the substrate, but by the precise opposite, the attracting of the pre-pupae by light, since the light source is arranged in such a manner that it illuminates the larva bridge and not the conveyor device, in particular, the conveyor belt. The pre-pupae strive to the light. This is advantageous, in particular, whenever the larvae have already developed into pre-pupae, since only at this stage do they strive towards the light instead of escaping therefrom.

It is preferably provided that the conveyor device, in particular, a conveyor belt of the conveyor device, is protected from light of the light source of the separating device. In particular, it is preferred that the conveyor device is not illuminated by the light source of the separating device and/or is protected from light, in particular, emanating from the light source of the separating device, and/or is darkened and/or arranged in a darkened region. It is preferred that the conveyor device receives and/or can receive less light than the larva bridge. This can preferably take place by shielding of the harvesting portion and/or by directing the light, with the result that as little light as possible appears on the conveyor belt. The illumination preferably has lenses which can specifically direct the light.

In particular, it is preferred that the harvesting ramp has a small slope in the direction of the conveyor belt such that the pre-pupae have to climb a harvesting ramp on the way to the light, i.e., have to migrate "upwards."

It has been found that the pre-pupae avoid sharp sheet-metal edges. It is, therefore, preferred for the larva bridge which is used for extracting the pre-pupae to have rounded edges. In particular, it has been shown that a rounding on the side facing away from the conveyor device, in particular, the conveyor belt, is particularly advantageous since a transfer to a pre-pupae transport belt thereby takes place in a particularly advantageous manner. The pre-pupae preferably move here from the conveyor device, on which substrate, which is still moist is located, to the light. On the way to the light, they preferably have to migrate over a larva bridge which is advantageously lowered onto the substrate in such a manner that it can be reached directly by the pre-pupae. For this purpose, the larva bridge preferably has a lowering mechanism. If the pre-pupae have then migrated along the entire section of the larva bridge, which runs transversely with respect to the direction of longitudinal extent of the conveyor device, as seen from the route of the pre-pupa, they preferably meet a sheet-metal edge which has been rounded, for example, by bevelling or crimping. A sharp-edged sheet-metal edge discourages the pre-pupae and they will not be animated to search for a path beyond the edge. A rounding can animate the pre-pupae to explore the further path. During this exploration, they preferably risk venturing ever further beyond the rounding until they can no longer keep their equilibrium and then fall over the rounded sheet-metal edge into the pre-pupa-collecting device and/or onto the pre-pupa transport belt, which is preferably designed as an endless conveyor. The rounding or bevelling is preferably configured in such a manner that the limb which extends from the bevelling in the direction of the floor is designed substantially perpendicularly in the extraction position. The angle of the bevelling is preferably selected in such a manner that the bevelled limb of the sheet-metal part points in the direction of the floor and is tilted beyond the perpendicular such that the pre-pupae cannot find any grip, and the rounding at which the larvae fall onto the collecting belt should be understood as a protrusion. Furthermore, preferably, the radius of the bevelling is greater than or equal to 1.5 mm. Even more preferably, the bevelling is a crimping with a radius of greater than or equal to 1.5 mm. In a further preferred form, the crimping provides the complete folding over of the sheet metal by 180°.

The larva bridge preferably has a certain minimum length, preferably of greater than 250 mm, as a result of which the pre-pupae run dry and are freed from adhering substrate residues. By means of the preferred provision of the larva bridge along the entire larva-separating portion, there is sufficient space for all of the pre-pupae, and, therefore, no blockage of the migrating pre-pupae occurs. It can, therefore, be achieved that the migrating drive of the pre-pupae is maintained. A possible pre-pupae blockage can, namely, have a disadvantageous effect on the migrating drive.

It has furthermore been found that the larvae can distribute the substrate over the entire belt width because of their movements, and thus would also carry the substrate on fixedly mounted larva bridges. In the case of a fixed mounting, the ramp would be in continuous contact with the substrate and would thereby be soiled. Furthermore, there would be the possibility of blockage of the substrate at the end side of the ramp facing the conveying direction. By means of the pivoting and/or folding of the larva bridges out of the substrate, a neater migration path is preferably, therefore, ensured, in particular, if the larva bridges are lowered only for the larva harvesting, in which the conveyor device is preferably at a standstill. The larva bridges can be lowered manually or automatically. It is preferred that the larva ramp is placed with a slight overlap with respect to the substrate.

The pre-pupae are preferably extracted in a portion provided for this purpose, in particular, the larva-separating portion. In order to ensure that the pre-pupae obtain sufficient time and are not unnecessarily interfered with during their migration, the conveyor device with the substrate is completely stopped for the extraction period. In a further step, the lowerable larva bridges are lowered onto the substrate such that the pre-pupae can climb without great difficulty onto the larva bridge and can move in the direction of the light source. After the extraction, the larva bridges are repositioned such that no substrate can remain adhering to the larva bridges when the conveyor device is switched on again.

A mechanical detaching device can be designed, for example, as a sieve, rinsing device, and/or vibration device.

The separating device, in particular, the larva bridge and/or the larva-collecting container, is preferably provided with a larva-attracting means, for example, with a nutrient attractive to larvae, a flavouring, and/or a scent.

The device preferably comprises two separating devices, wherein the two separating devices are preferably designed differently and/or one is connected downstream of the other.

The first separating device preferably comprises a light source, a larva bridge, and a larva-collecting container and, optionally, a residual-excrement-collecting container. The second separating device, which is connected downstream, preferably comprises a mechanical detaching device, such as, for example, a sieve or a rinsing device, and a larva-collecting container and, optionally, a residual-excrement-collecting container.

Furthermore, it is preferred that the conveyor section, in particular, the larva-introducing portion, has a liquid-introducing portion and/or a mixing portion.

Water is preferably provided as the liquid. The liquid is preferably output from a liquid reservoir via an atomizer, spray head, drip tube, and/or nozzle tube in the form of drops or spray mist, as a result of which uniform moistening is preferably obtained.

It has been found that pre-pupae likewise have a sense for moisture or substrate moisture. At the pre-pupa stage, the larvae avoid moist substrate (for example, for >25% moisture) since they strive to reach dry areas so that they are not destroyed by fungi after pupation. This effect can additionally be used in order to drive the bugs out of the substrate, specifically by the harvesting portion being remoistened in addition to being illuminated.

The mixing portion can be designed, for example, as an intermediate conveyor with a high conveying speed, in particular, a conveying speed which is higher than that of the conveyor section. In particular, the mixing portion serves to achieve a conversion and/or mixing of the animal excrement mixed with larvae and/or larva eggs.

The device preferably comprises a control device that is designed to determine: a quantity of larvae and/or larva eggs to be metered in depending on one or more process parameters, a quantity of animal excrement to be metered in depending on one or more process parameters, a quantity of liquid to be metered in depending on one or more process parameters, and/or a quantity of further resources to be metered in, such as, for example, nutrients for the larvae and/or larva eggs, depending on one or more process parameters.

Process parameters can be, in particular, quantity and properties, such as, for example, dry substance (TS) content or the like of excrement in various process phases (in particular, of the initial excrement, of the excrement consumed by the larvae, and of the residual excrement), ambient parameters (such as, for example, temperature and/or air humidity), length of the conveyor section, device throughput, or the like. The device preferably comprises one or more sensors for determining one or more process parameters. The control device is preferably designed to receive process parameter data, preferably from one or more sensors.

Furthermore, preferably, a larva-metering device is provided that is designed to meter in a certain quantity of larvae and/or larva eggs depending on one or more process parameters and/or depending on a quantity of larvae that is determined by the control device and is to be metered in.

The metering in of the young larvae is preferably possible manually or in an automated manner. Storage of a certain quantity of young larvae by means of a storage container, which is preferably designed as a hopper, is preferably provided in this case. An agitating means is preferably located at the bottom of the storage container and feeds the young larvae to an exit point and prevents clogging. Said agitating means is preferably designed in such a manner that young larvae are not squashed, but clumping is prevented. This is achieved by the preferable use of one or more agitator fingers, preferably agitator blades composed of flexible material. Furthermore, angled agitator blades for worm-like agitating movement are preferred since, in the case of vertical blades, there is the risk of clumping and squashing of the young larvae.

The agitating speed can preferably be variably configured and preferably permits adaptation to different larva batches (with regard to moisture and therefore clumping tendency) and also to the belt progress of the conveyor device. The outlet opening is adjustable in size, preferably manually or in an automated manner, in order thereby also to prevent squashing of the larvae. The outlet opening can also be designed to be completely closable. A multiple arrangement of the outlet openings can furthermore be preferred since a homogeneous, more uniform distribution of the larvae on the substrate can thereby be achieved.

A larva-distributing means is preferably located below the outlet opening and serves to apply the larvae uniformly to the substrate. This can be designed, for example, as a rotating plate with corner brackets screwed thereon, preferably in a radially symmetrical arrangement for the radially symmetrical distribution. It is also conceivable for the corner brackets to be adjustable relative to the spreading axis, in or counter to the spreading direction, in order to set the spreading pattern. A further preferred embodiment makes provision for variable setting of the rotation speed of the plate in order to set the spreading width, in a manner corresponding to the belt width. Operation with variable belt widths is, therefore, made possible. This distribution principle of fertilizer spreaders is generally known.

In a further preferred embodiment, an animal-excrement-metering device is provided that is designed to meter in a certain quantity of animal excrement depending on one or more process parameters and/or depending on a quantity of animal excrement that is determined by the control device and is to be metered in.

A distributing and/or comminuting device for animal excrement, which is also referred to here as substrate, is preferably provided. The distribution and comminution of the substrate preferably take place by means of driven worms. Subsequent sliders and speed control of the conveyor device preferably permit different substrate heights.

Furthermore, preferably, the device comprises a liquid-metering device that is designed to meter in a certain quantity of liquid depending on one or more process parameters and/or depending on a quantity of liquid that is determined by the control device and is to be metered in.

A preferred development is distinguished in that at least one region of the conveyor section is arranged in an excrement-drying device. Furthermore, it is preferred that various regions of the conveyor section are arranged in different excrement-drying devices.

The excrement-introducing portion and the mixing portion are preferably designed as an individual portion of the conveyor section. The excrement-introducing portion and the mixing portion can be designed as one and the same portion, wherein said one portion then carries out two functions; in particular serves both as an excrement-introducing portion and as a mixing portion.

The device for residue use in livestock farming is preferably arranged in a climate-controlled room. The device for residue use in livestock farming preferably has a housing, for example a 40-foot container, in particular, also in the form of a high cube variant which forms the climate-controlled room. The device for residue use in livestock farming is preferably entirely or partially arranged in the housing, in particular, in a transport state. Simple transport of the device for residue use in livestock farming is thereby also possible. The climate-controlled room permits independency with respect to the climatic ambient parameters, such as, for example, temperature and air humidity. The climate-controlled room is preferably correspondingly insulated and/or able to be conditioned climatically with a device for regulating the climate and also with air-conditioning units, i.e., for example, cooling/heating, ventilation, and/or dehumidification/humidification. Furthermore, it is preferred for one of the climate parameters to be regulated depending on the substrate temperature such that ideal growth conditions for the larvae can be set. The measurement of the ammonia content of the air and ventilation control, which is correspondingly dependent thereon by aerating the ammonia gases, is furthermore preferred.

The device for residue use in livestock farming preferably has a plurality of planes, as a result of which conversion and mixing can take place, and also ventilation of the substrate.

An exemplary embodiment, not meant to be limiting, is as follows: Because of the animal-excrement-metering device, the first plane is half the length of remaining planes, as a result of which there is a higher quantity of substrate in relation to the belt length of the plane. The higher quantity of substrate and resulting anaerobic regions give rise to slight heating which is ideal for young larvae, the metabolic energy of which is not yet sufficient to heat the substrate. The second to fourth plane is approximately twice the length of the first plane, as a result of which the growth of the larvae is taken into account since an increased space requirement for the growing larvae arises because of the rapid growth (40 times length growth).

As a process management example:

$1^{st}$ (preferably uppermost) plane: Young larvae of the age of four to seven days;

$2^{nd}$ plane: More space for larvae of the age of seven to ten days;

$3^{rd}$ plane: Larvae of the age of ten to thirteen days; and $4^{th}$ (preferably lowermost) plane: Larvae of the age of thirteen to fifteen days and development to pre-pupa, and also migration thereof.

Thus, adapting the routine in accordance with the development of the larvae in a different substrate is preferred.

Different speeds of the belts with means, such as, for example, frequency converters, are possible in order to permit different substrate heights and/or longer residence periods in the lowermost stage (harvesting stage). The pre-pupae are preferably located only in the lowermost plane.

According to a further aspect of the invention, the object mentioned at the beginning is achieved by a system for residue use in livestock farming, comprising a previously described device for residue use in livestock farming, one or more first excrement-drying devices, and a second excrement-drying device, wherein regions of the conveyor section of the device for residue use are designed as drying belts of the one or more first excrement-drying devices and of the second excrement-drying device, wherein the larva-introducing portion is arranged in the first excrement-drying device, wherein the excrement-introducing portion is arranged between the first and the second excrement-drying device and/or between a plurality of first excrement-drying devices, and wherein the larva-separating portion is arranged in the second excrement-drying device and/or is arranged downstream of the second excrement-drying device.

A preferred refinement of the system for residue use in livestock farming makes provision for the mixing portion to be arranged between the first and the second excrement-drying device and/or between a plurality of first excrement-drying devices.

According to a further aspect of the invention, the object mentioned at the beginning is achieved by a method for residue use in livestock farming, preferably by means of a previously described device for residue use in livestock farming, the method comprising: conveying animal excrement along a conveyor section, wherein the conveyor section has a larva-introducing portion, an excrement-introducing portion and a larva-separating portion; metering in larvae and/or larva eggs in the larva-introducing portion; metering in animal excrement in the excrement-introducing portion depending on one or more process parameters; and separating the larvae in the larva-separating portion.

These further aspects and their possible developments have features or method steps which make them suitable in particular to be used for or with a device for residue use in livestock farming and the developments thereof.

With regard to the advantages, variant embodiments, and embodiment details of said further aspects of the invention and the developments thereof, reference is made to the preceding description of the corresponding device features.

BRIEF DESCRIPTION OF THE DRAWINGS

Preferred embodiments of the invention will be described by way of example with reference to the attached figures, in which.

DETAILED DESCRIPTION OF THE EMBODIMENTS

In the Figures, the same or corresponding elements or units are each provided with the same and/or the corresponding reference signs. When an element or a unit has already been described with reference to a particular Figure, a detailed description is dispensed with when discussing another Figure. However, it is to be understood that the present disclosure may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Figure 1:
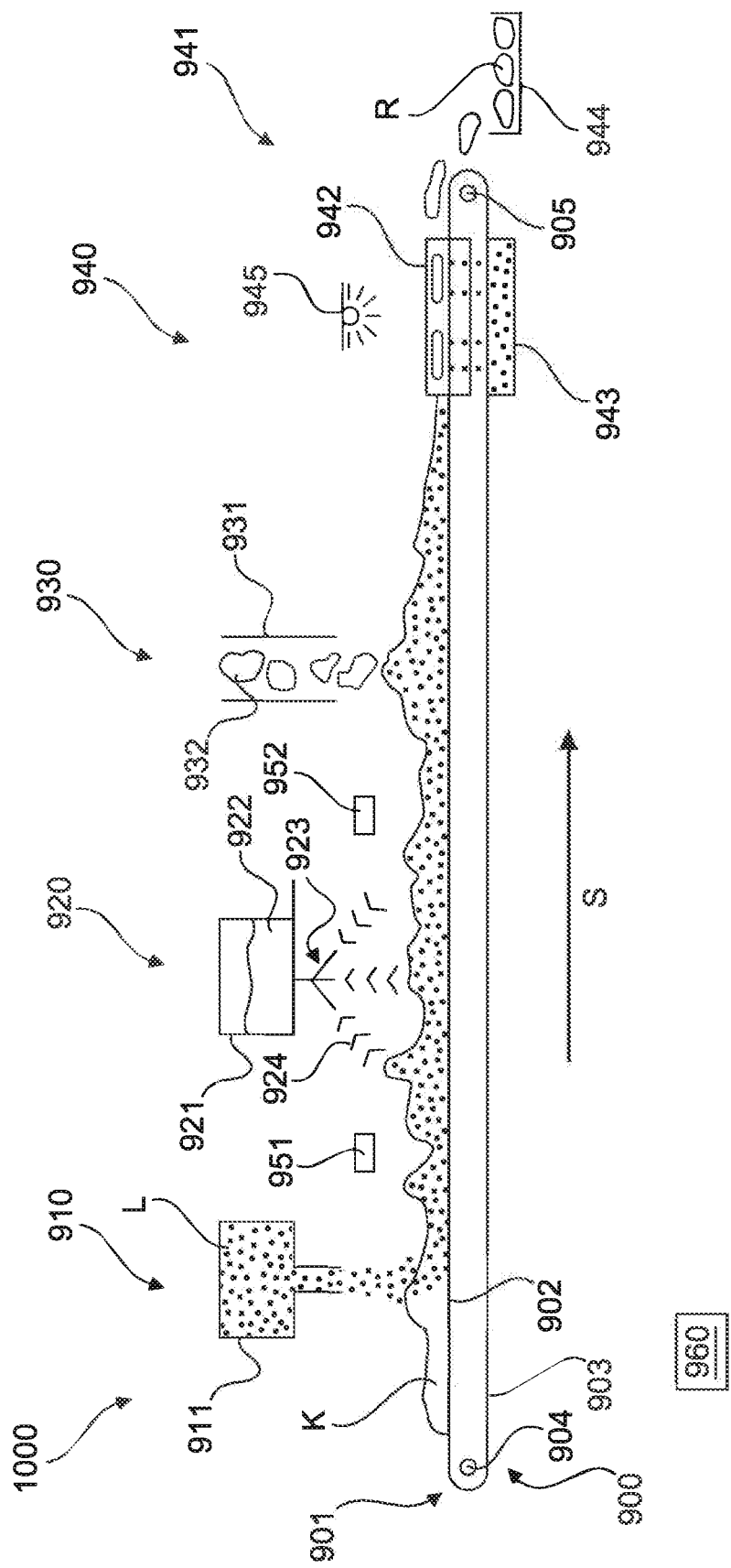
FIG. 1 shows a schematic illustration of an example of a device for residue use in livestock farming.

An example of a device 1000 for residue use in livestock farming is illustrated by way of example and schematically in FIG. 1.

FIG. 1 shows a device 1000 for residue use in livestock farming with a conveyor device 900 for conveying animal excrement K along a conveyor section S. The conveyor device 900 is designed as a belt conveyor with an endless belt 901 with a carrying run 902, on which the excrement K is conveyed, and a return run 903, which runs are deflected by deflecting pulleys 904, 905. One of the deflecting pulleys 904, 905 is preferably driven electrically.

The conveyor section S has a larva-introducing portion 910 for metering in larvae and/or larva eggs L, a liquid-introducing portion 920 for metering in liquid 922, an excrement-introducing portion 930 for metering in animal excrement K depending on one or more process parameters, and a larva-separating portion 940 for separating the larvae L. The larvae and/or larva eggs L can be metered in from a larva reservoir 911. The liquid 922, in particular, water, can be output from a liquid reservoir 921 in the form of drops or spray mist 924 via an atomizer or spray head 923. The excrement 932 to be metered in can be supplied in the excrement-introducing portion 930 via an excrement-supply means 931, preferably likewise a belt conveyor (not shown).

One or more sensors 951, 952 which detect one or more process parameters, are preferably provided in the device 1000. Quantities of larvae and/or larva eggs L, liquid 922, and/or excrement 932 to be metered in can preferably be determined from said process parameters by a control device 960.

A separating device 941 with a larva-collecting container 943 and a residual-excrement-collecting container 944 is arranged in the larva-separating portion 940. The separating device 941 furthermore has a light source 945 which illuminates the larva-separating portion 940. A larva bridge 942 leads from the larva-separating portion 940 to the larva-collecting container 943. An interior of the larva-collecting container 943 is preferably protected from light of the light source 945. The larvae L in the larva-separating portion 940 are thereby excited to leave the illuminated region and to pass via the larva bridge 942 into the larva container 943, preferably by their own movement. The larvae L can thereby be particularly simply detached from the residual excrement R.

Figure 2:
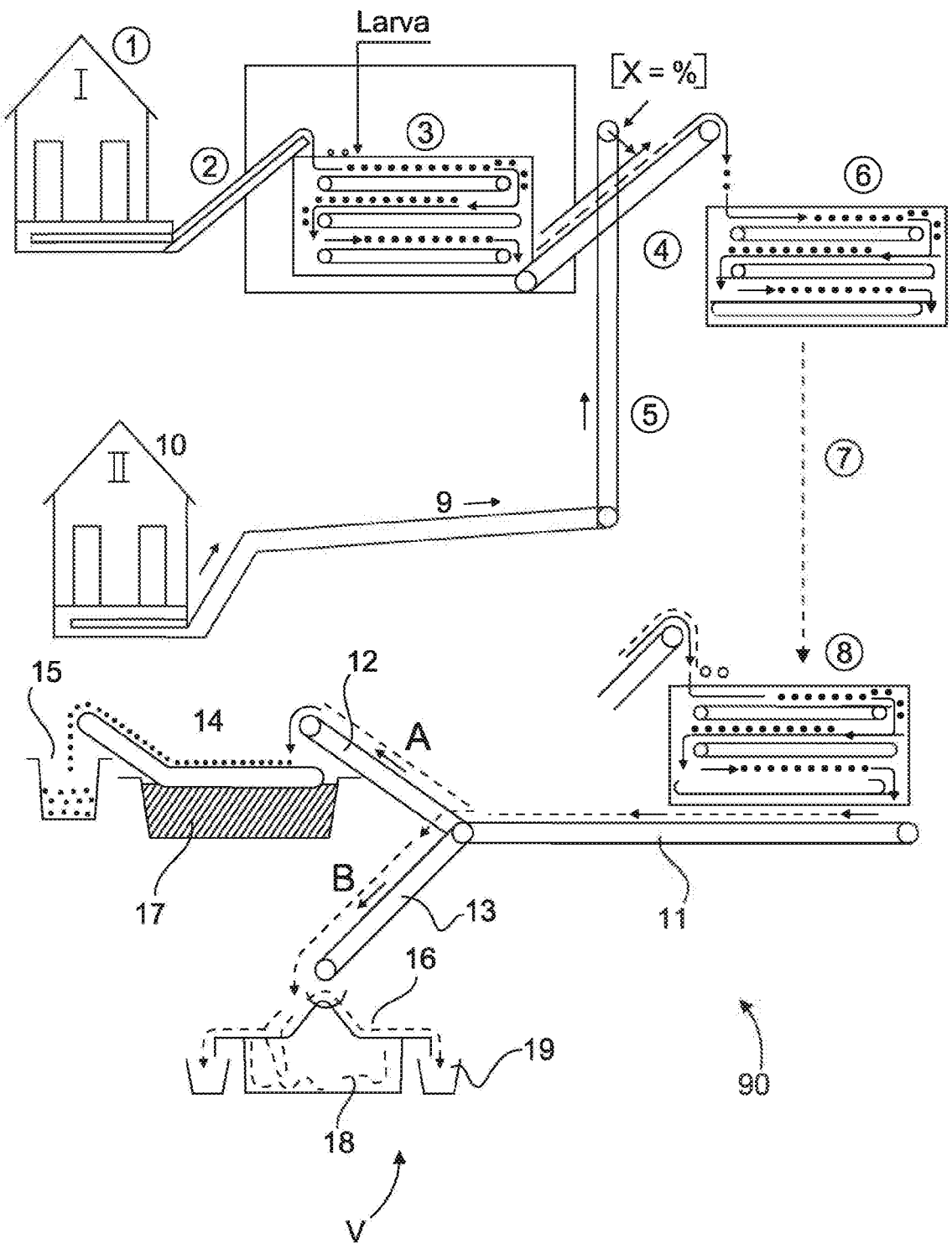
FIG. 2 shows a schematic sequence diagram of an example for a method for residue use in livestock farming with a device for residue use in livestock farming.

FIG. 2 shows a schematic sequence diagram of an example of a method V for residue use in livestock farming with a device 90 for residue use in livestock farming.

Figure 3:
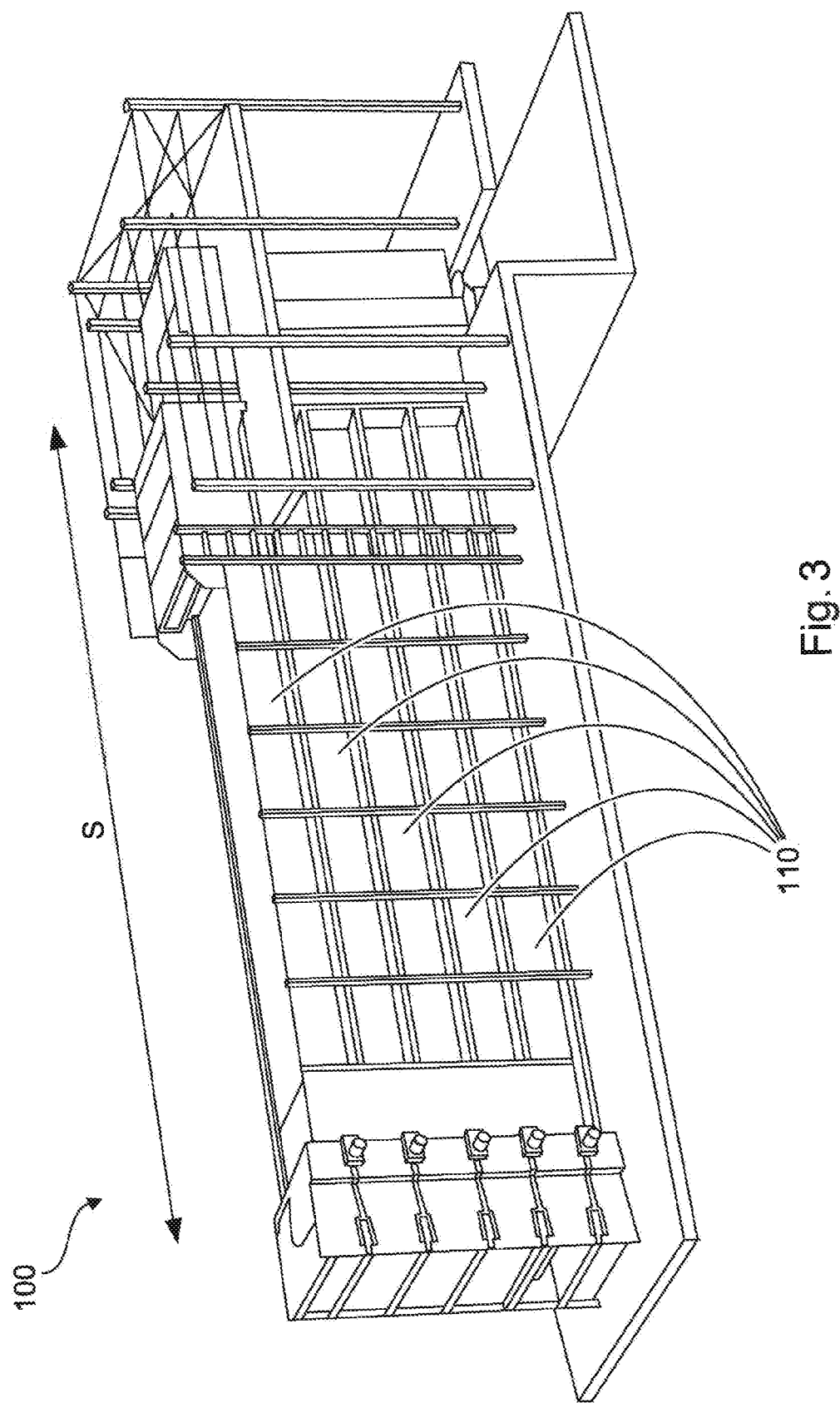
FIG. 3 shows a three-dimensional view of an excrement-drying device.
Figure 4:
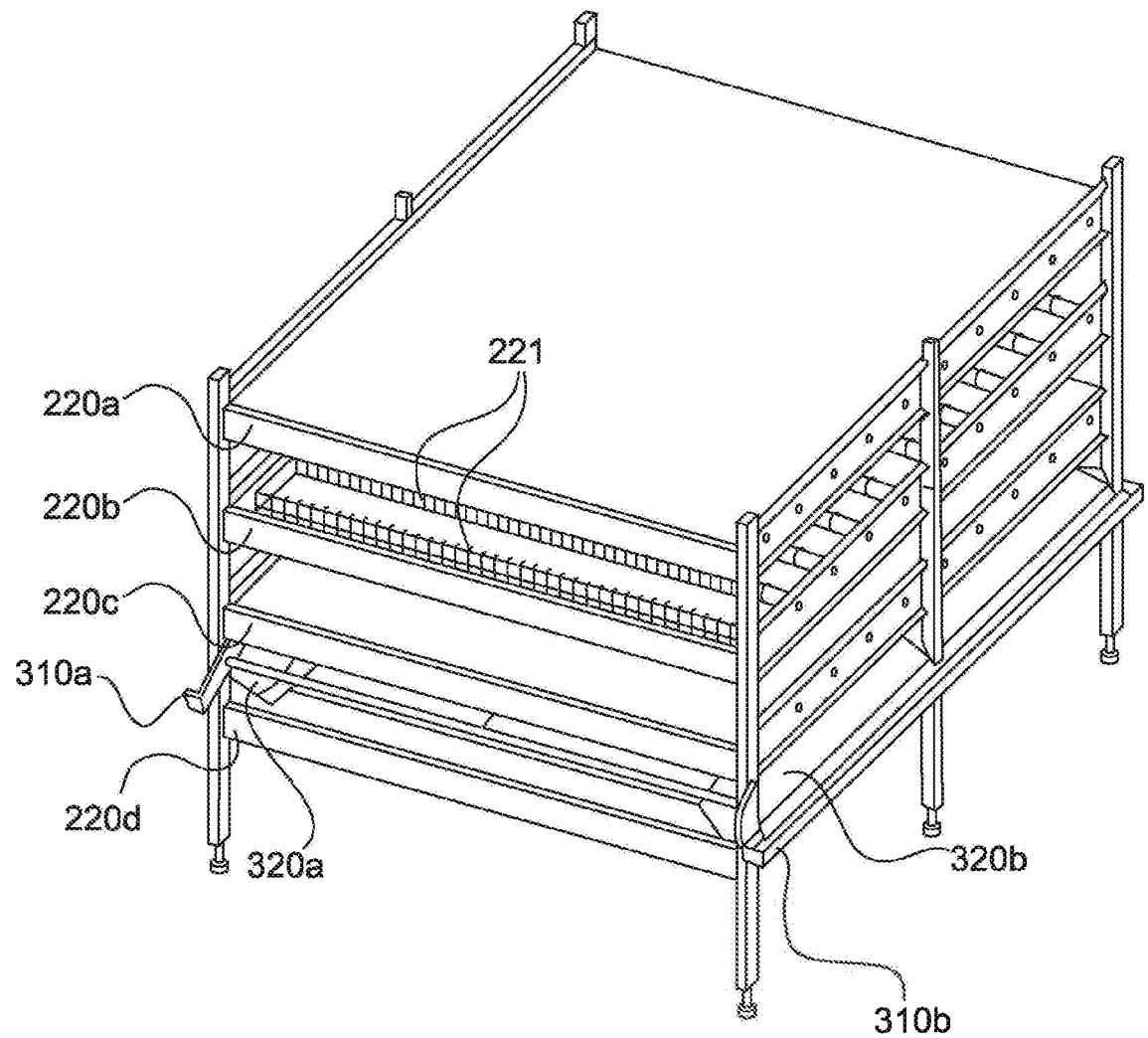
FIG. 4 shows a three-dimensional view of part of an exemplary device for residue use in livestock farming.
Figure 5:
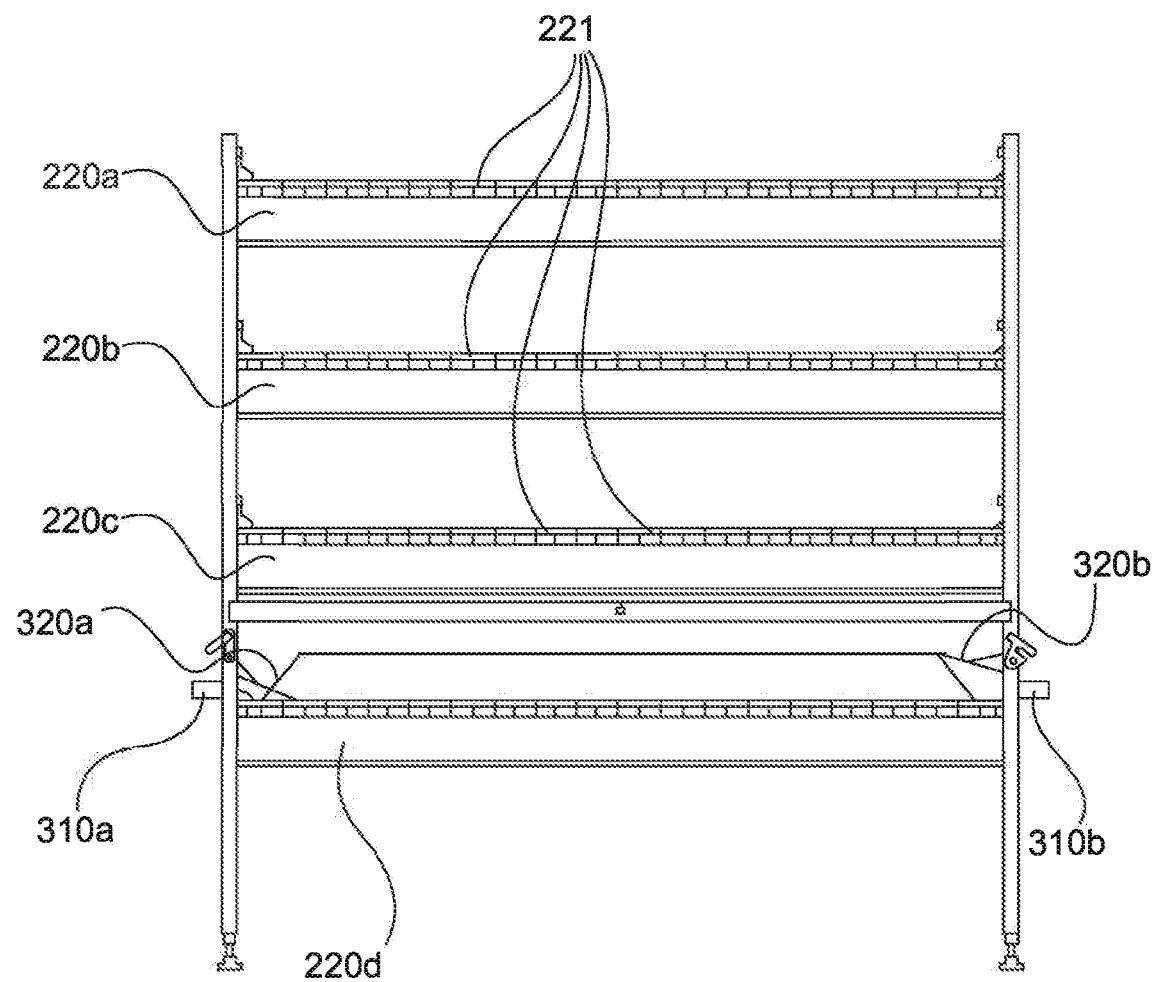
FIG. 5 shows a front view of the device according to FIG. 2.
Figure 6:
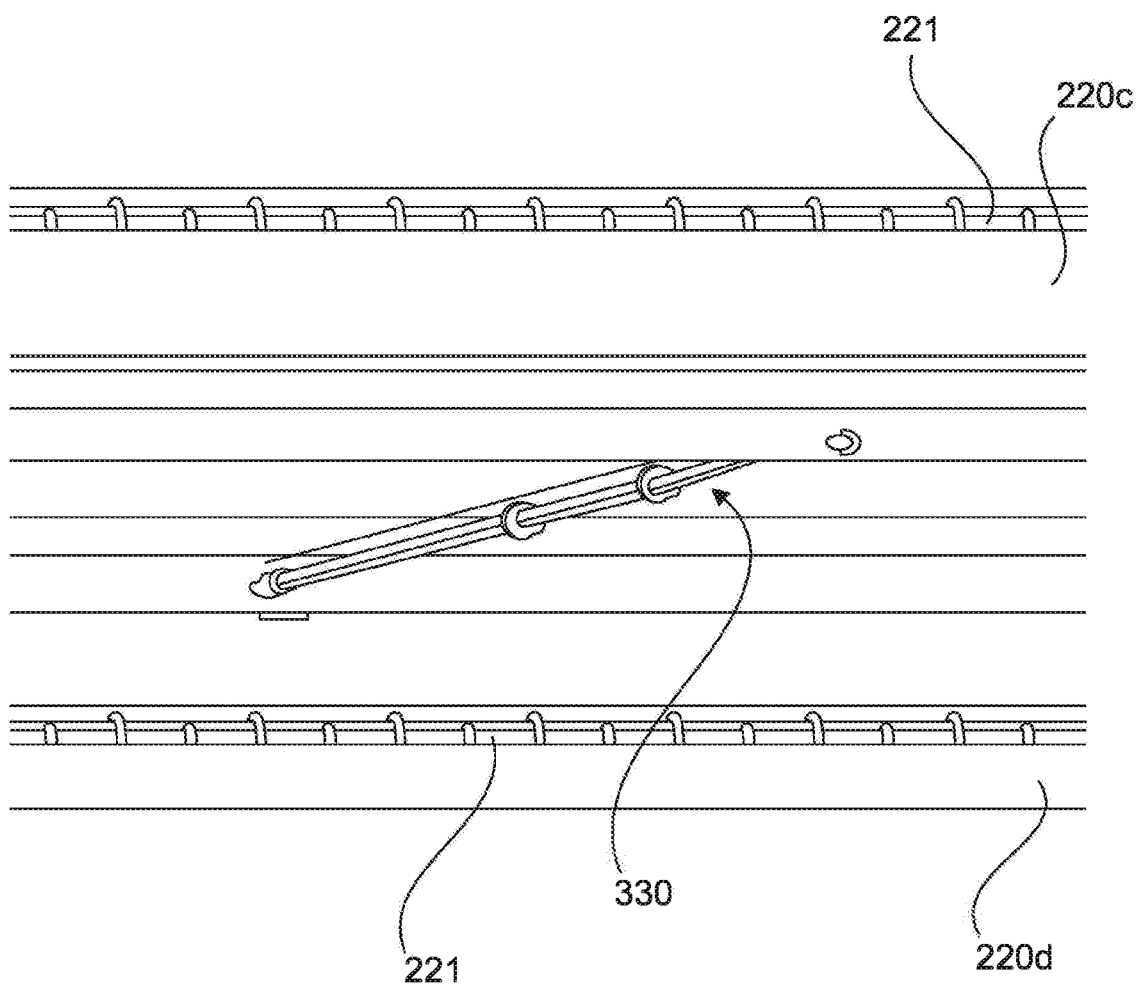
FIG. 6 shows a detailed perspective illustration of the separating device which is shown.
Figure 7:
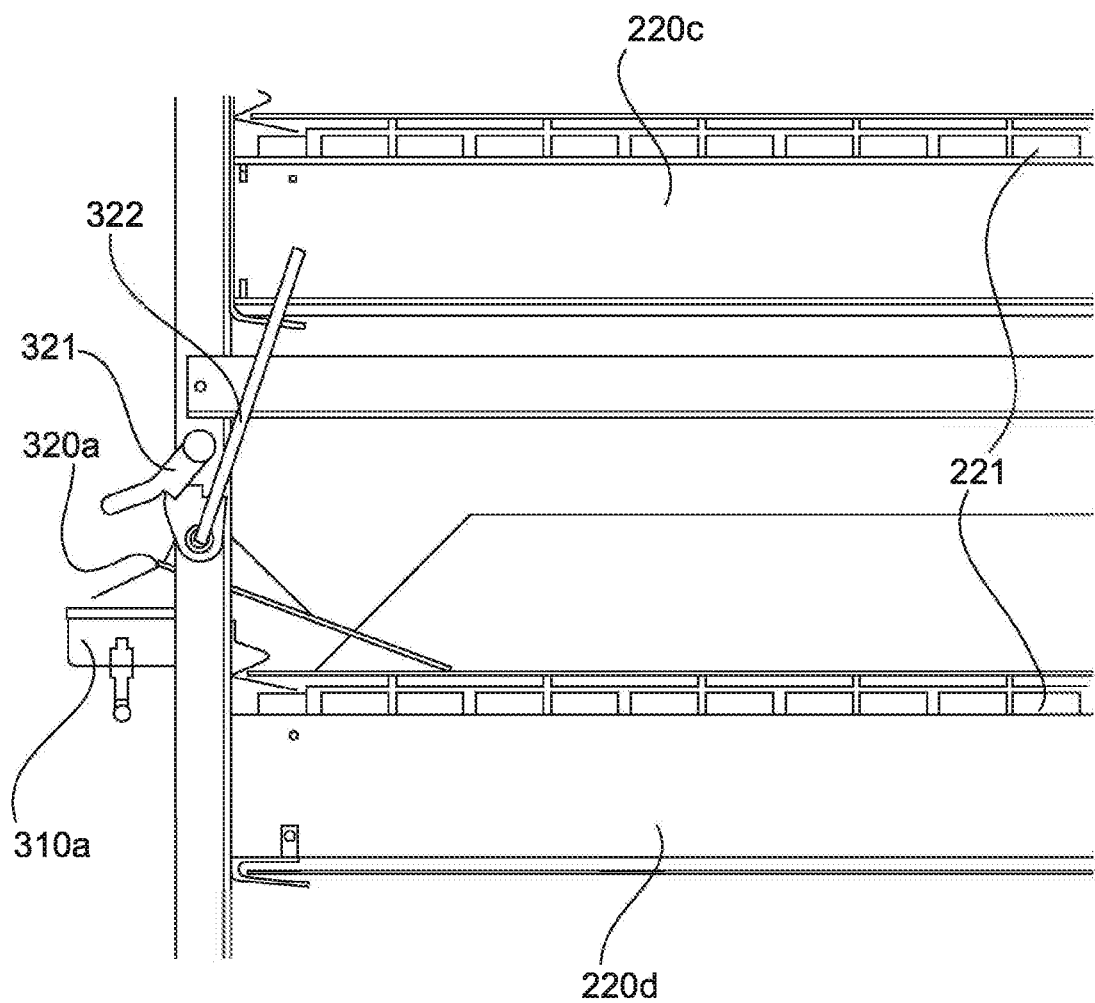
FIG. 7 shows a detailed illustration of the light source of the separating device shown in FIG. 1.

FIG. 3 shows a three-dimensional view of an excrement-drying device 100 with five tiers 110. The conveyor section S, which is merely indicated schematically in FIG. 3, extends via opposed, driven conveyor devices in the tiers which are located one above another. The tier arrangement also affords the advantage that, during the transfer of the excrement and larvae mixture between the tiers, circulation takes place by falling onto the lower tier and, therefore, exposes usable material (excrement) to the larvae. A plurality of such excrement-drying devices 100 can be positioned in a row and together form a conveyor section for a device for residue use in livestock farming. The number of required excrement-drying devices 100 varies depending on the quantity of the animal excrement to be dried and/or of the larvae to be cultivated.

Figure 8:
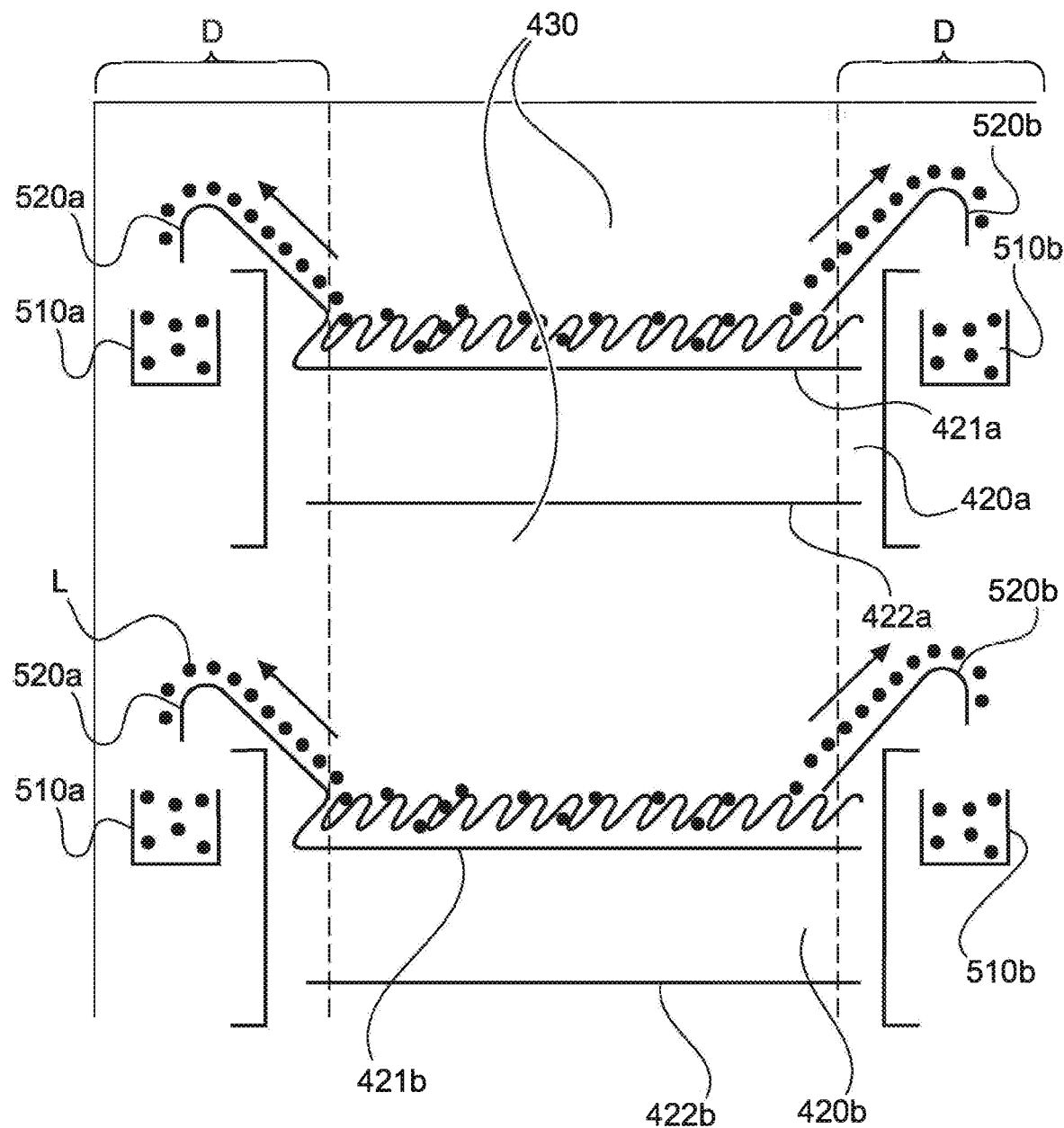
FIG. 8 shows a schematic illustration of part of an exemplary device for residue use in livestock farming with a separating device.

FIGS. 4 through 8 illustrate possibilities of separating devices in more detail. The conveyor section extends in the regions shown in FIGS. 4 through 8 over a plurality of planes 220a, 220b, 220c, 220d, and 420a, 420b. In FIG. 8, the carrying run 421a, 421b and the return run 422a, 422b of the belt conveyors can be seen in each case in the two planes 420a, 420b. The bearers 221 of the belt conveyors can be seen in FIGS. 4 through 7.

During the harvesting of the larvae in the last excrement-drying device, a separating device with a light source 330, 430 can be used for controlling the movement of the larvae. In principle, this approach makes use of the light sensitivity of the larvae. The light source 330, 430 illuminates the larva-separating portion of the conveyor section preferably exclusively or substantially.

To harvest the larvae, larva-collecting containers 310a, 310b, and 510a, 510b are arranged at the sides of the conveyor section at the distance D. The larvae L can pass via larva bridges 320a, 320b, and 520a, 520b, which are designed in the form of plates, into the larva-collecting containers 310a, 310b, and 510a, 510b, preferably by means of their own movement, which is caused or assisted by the light source 330, 430. The larva bridges can be configured so as to be movable from a position 320a, in which the larvae can pass via the larva bridges 320a into the larva-collecting containers 310a, into a position 320b, in which this is not provided, and back. For example, the beginning and end of the larva harvesting can thus be controlled, preferably, for example, in coordination with the operation of the light source. In the position 320b, the conveyor device, in particular, the excrement belt on which the excrement and the larvae lie, preferably still remains movable and can, therefore, be driven. For this purpose, the larva bridge is preferably raised in the position 320b. A lowering mechanism is preferably provided, preferably in the form of an adjustment and/or fixing means, in order to adjust and/or fix the larva bridge, which is designed here as a metallic side plate, for controlling the movement of the larvae into or in the position 320a, 320b. The adjustment and/or fixing means preferably has an adjustment mechanism 322, for example, a lever. The adjustment mechanism 322 is designed, in particular, to bring the larva bridge from the position 320a into the position 320b and/or vice versa. Furthermore, preferably, the adjustment and/or fixing means has a fixing mechanism 321, for example, a hook, which is designed in particular to fix the larva bridge in the position 320b.

The method V, which is illustrated schematically in FIG. 2, for residue use in livestock farming, explained in more detail below, with a device 90 for residue use in livestock farming. The poultry excrement originating from a first poultry house I, 1 is supplied via a feed device 2 to a first excrement-drying device 3 and distributed over the entire width of the drying belt. Via a continuous supply, the entire conveyor section is thus ultimately filled with poultry excrement. In the example shown in FIG. 2, the first excrement-drying device 3 corresponds to the larva-introducing portion. Larvae and/or larva eggs are introduced here into the excrement in a specific mixing ratio.

The animal excrement including larvae and/or larva eggs is transported by the driven excrement belt of the belt conveyor of the conveyor device through the first excrement-drying device 3. Owing to the nutrient consumption by the larvae, the quantity of excrement is reduced. As soon as the first excrement-drying device 3 has been passed through, the animal excrement is conveyed via a mixing portion 4 to a second excrement-drying device 6. The mixing portion 4 is designed identically here to an excrement-introducing portion where further animal excrement is supplied from a second poultry house II, 10 via feed devices 9, 5. This metering in of animal excrement, for example X % of the initial amount of excrement, takes place in order to ensure sufficient availability of food for the larvae and/or larva eggs and therefore optimum growth, and preferably depending on one or more process parameters.

The supply of animal excrement does not have to take place directly from a livestock stall. Intermediate storage of the animal excrement or a decentral solution are likewise possible.

This process, the mixing and supply of new animal excrement between two drying devices, can be repeated several times. What is decisive for the number of repetitions is, inter alia, the quantity of animal excrement to be processed, the growth time of the larvae and/or larva eggs, and the sought quantity of larva production. The process can be scaled at this point, in particular, by the fact that a variable number of excrement-drying devices 7 (merely indicated schematically in FIG. 2) can be added.

The final excrement-drying device 8 differs from the upstream excrement-drying devices, in particular, by means of the larva-separating portion for separating the larvae, in particular, by means of the separating device. This is shown in more detail in FIGS. 3 to 8 and described in more detail there.

If not all of the larvae can be harvested by means of light control, one or more further separating devices can be connected downstream. For this purpose, the residual material consisting of residual excrement and remaining larvae, which is located in the final excrement-drying device 8, can first be discharged via a further conveyor system 11. Subsequent harvesting of the larvae remaining in the residual excrement can take place via the following two options:

A—Harvesting by means of washing: In this case, the residual excrement with the remaining larvae is conveyed via a feed device 12 to a rinsing device 14 and rinsed out there. Residual excrement, which has been rinsed out, is collected, together with the washing liquid or separately therefrom, in a residual-excrement-collecting container 17, and the cleaned larvae are collected in a larva-collecting container 15.

B—Harvesting by means of sieving: In this case, the residual excrement with the remaining larvae is conveyed via a feed device 13 to a sieve 16 where the larvae are sieved off and collected via drawers 18 below the sieve 16. The remaining residual excrement is discharged into residual-excrement-collecting containers 19.

Figure 9:
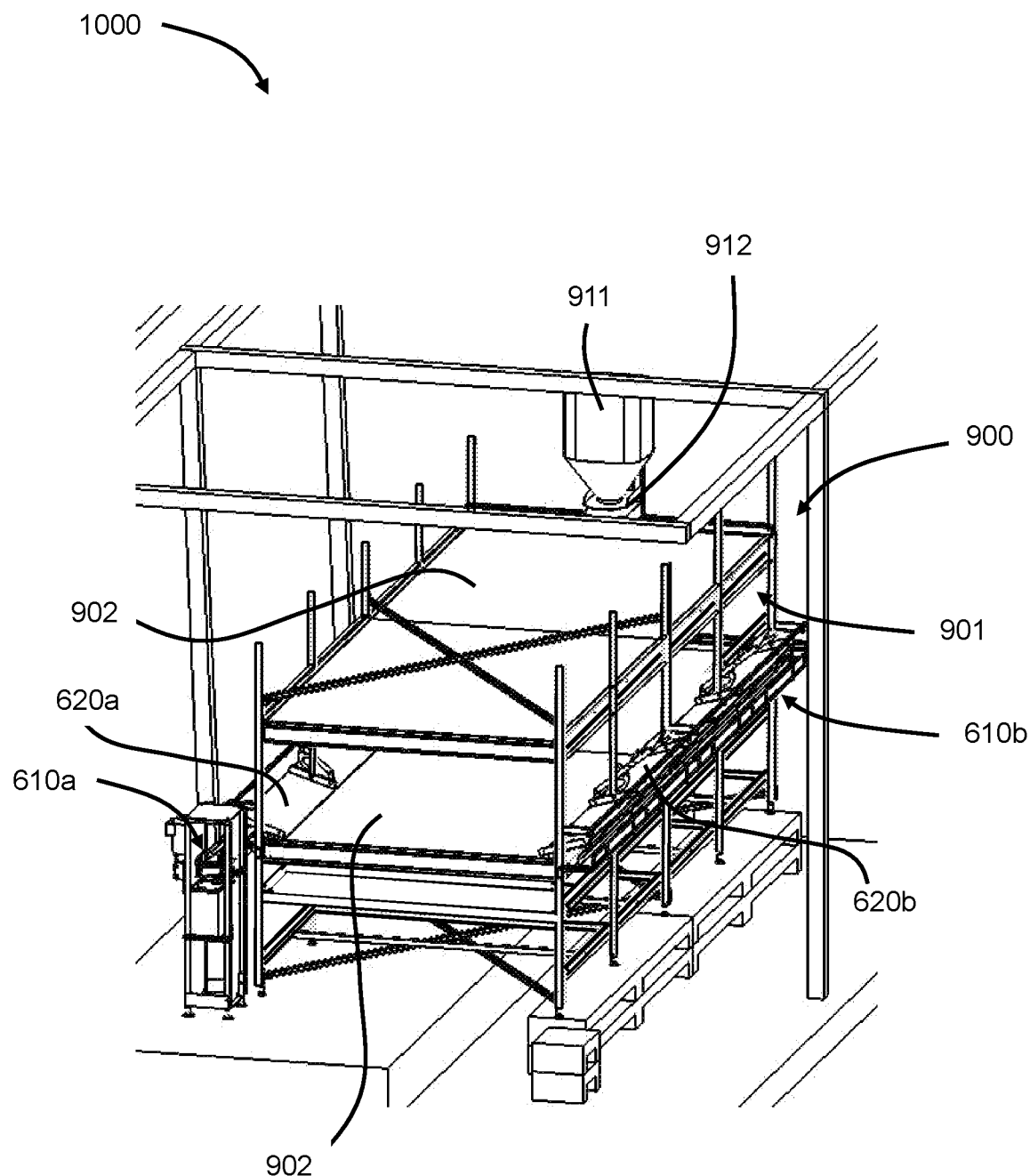
FIG. 9 shows a schematic illustration of an exemplary device for residue use in livestock farming.
Figure 10:
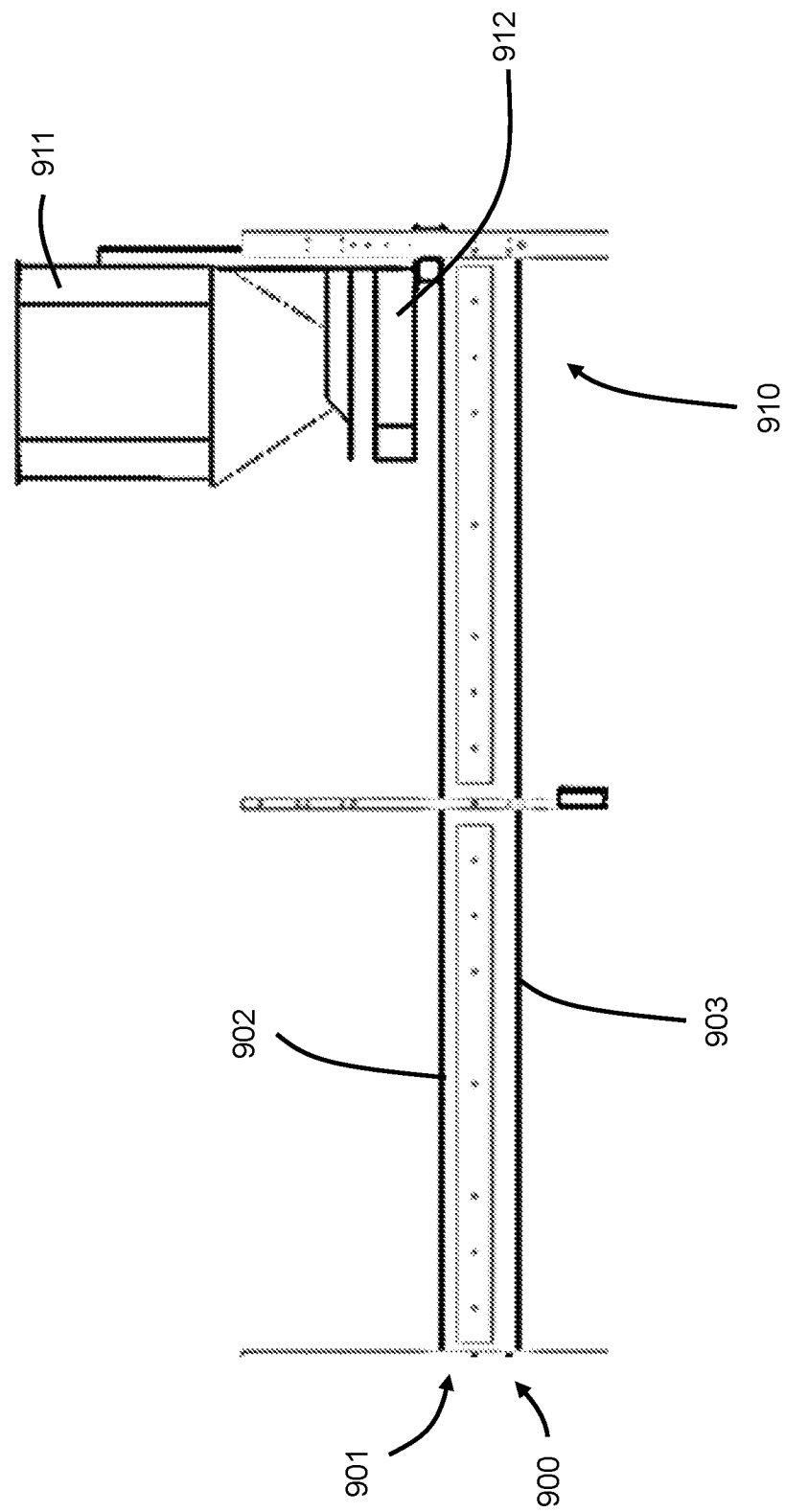
FIG. 10 shows an enlarged detail from FIG. 9.
Figure 11:
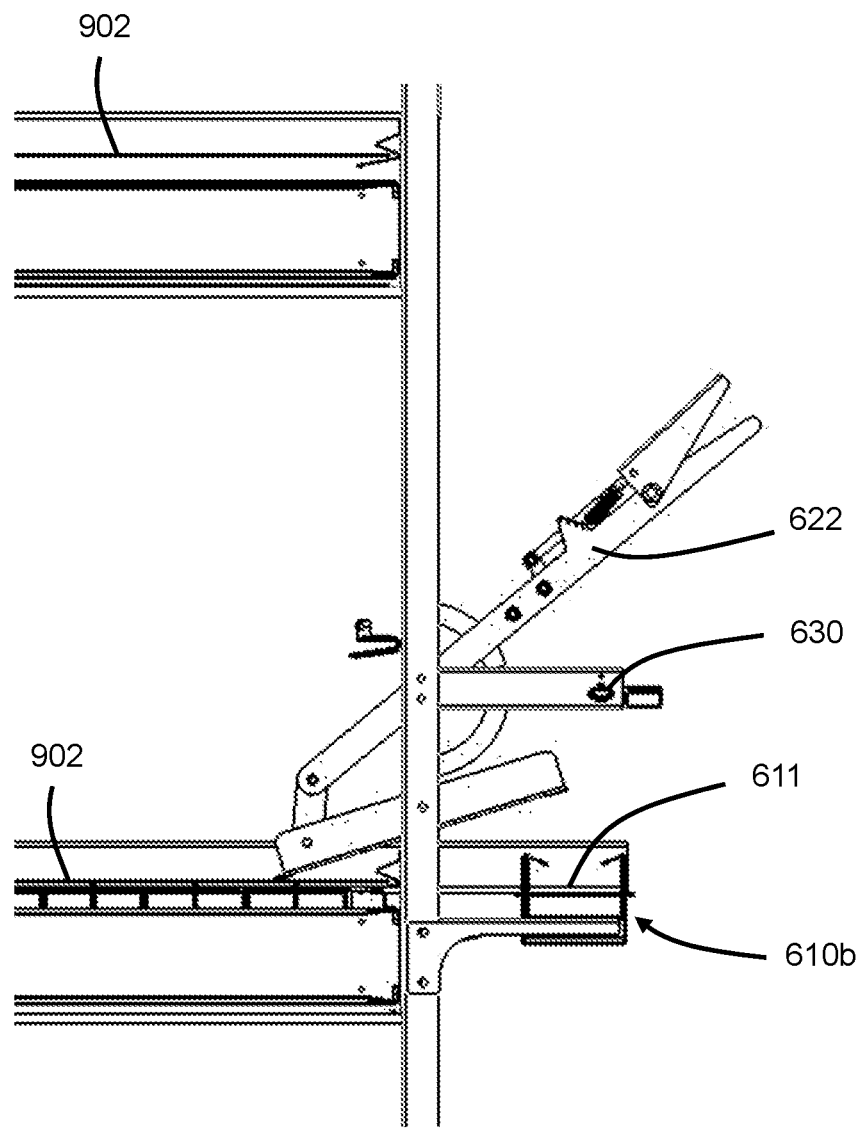
FIG. 11 shows a further enlarged detail from FIG. 9.

FIGS. 9-11 schematically illustrate a further example of a device 1000 for residue use in livestock farming. The device 1000 for residue use in livestock farming has a conveyor device 900, which is designed as a belt conveyor, with an endless belt 901 having a carrying run 902 and a return run 903 for conveying animal excrement along a conveyor section.

A larva reservoir 911 and a larva-distributing means 912 are arranged in the larva-introducing portion 910 for metering in young larvae.

In order to harvest the larvae at the pre-pupa stage, larva-collecting containers 610a, 610b, here in the form of U-shaped larva channels with larva transport belts 611, are arranged at the sides of the conveyor section. The pre-pupae can pass via larva bridges 620*a*, 620*b*, which are designed as plates with rounded edges, into the larva-collecting containers 610*a*, 610*b*, preferably by means of their own movement, which is caused or assisted by the light source 630. The larva bridges can be configured to be movable by means of an adjustment means 622, which is designed as a lowering mechanism, from the lowered position, which is illustrated in FIG. 11, and in which the larvae can pass via the larva bridges 620*a* into the larva-collecting containers 610*a*, into a raised position, in which this is not provided, and back. For example, the beginning and end of the larva harvesting can thus be controlled, preferably in coordination with the operation of the light source 630. The light source 630 is arranged to illuminate the larva bridge 620*a*, but not the carrying run 902 of the conveyor belt 901.

It will be understood by one having ordinary skill in the art that construction of the described present disclosure and other components is not limited to any specific material. Other exemplary embodiments of the disclosure disclosed herein may be formed from a wide variety of materials, unless described otherwise herein.

For purposes of this disclosure, the term "operably coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "operably connected" (in all of its forms, connect, connecting, connected, etc.) generally means that one component functions with respect to another component, even if there are other components located between the first and second component, and the term "operable" defines a functional relationship between components.

It is also important to note that the construction and arrangement of the elements of the present disclosure as shown in the exemplary embodiments is illustrative only. Although only a few embodiments of the present innovations have been described in detail in this disclosure, those skilled in the art who review this disclosure will readily appreciate that many modifications are possible, e.g., variations in sizes, dimensions, structures, shapes and proportions of the various elements, values of parameters, mounting arrangements, use of materials, colors, orientations, etc. without materially departing from the novel teachings and advantages of the subject matter recited. For example, elements shown as integrally formed may be constructed of multiple parts or elements shown in multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of the wide variety of materials that provide sufficient strength or durability, in any of the wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the aforementioned structure and method without departing from the concepts of the present disclosure, and further it is to be understood that such concepts are intended to be covered by the following claims unless these claims by their language expressly state otherwise.

The invention claimed is:

1. A device for residue use in livestock farming, comprising:
   a conveyor device for conveying animal excrement along a conveyor section, wherein the conveyor section has a larva-introducing portion for metering in larvae and/or larva eggs, an excrement-introducing portion for metering in animal excrement depending on one or more process parameters, and a larva-separating portion for separating the larvae; and
   a separating device comprising a light source and a larva bridge;
   wherein the light source is adapted to illuminate the larva bridge.

2. The device pursuant to claim 1, wherein the separating device comprises a larva-collecting container.

3. The device pursuant to claim 1, comprising a residual-excrement-collecting container.

4. The device pursuant to claim 1, wherein the light source is arranged parallel to the direction of longitudinal extent of the larva-separating portion.

5. The device pursuant to claim 1, wherein the conveyor device comprises a conveyor belt protected from light of the light source of the separating device.

6. The device pursuant to claim 1, further comprising two separating devices, wherein the two separating devices are designed differently and/or one is connected downstream of the other.

7. The device pursuant to claim 1, wherein the larva-introducing portion of the conveyor section has a liquid-introducing portion and/or a mixing portion.

8. The device pursuant to claim 1, further comprising a control device designed to determine:
   a quantity of larvae and/or larva eggs to be metered in depending on one or more process parameters;
   a quantity of animal excrement to be metered in depending on one or more process parameters; and/or
   a quantity of liquid to be metered in depending on one or more process parameters.

9. The device pursuant to claim 8, further comprising:
   a larva-metering device designed to meter in a certain quantity of larvae and/or larva eggs determined by the control device depending on one or more process parameters and/or depending on a quality of larvae and/or larva eggs which is determined by the control device and is to be metered;
   an animal-excrement-metering device which is designed to meter in a certain quantity of animal excrement depending on one or more process parameters and/or depending on a quantity of animal excrement which is determined by the control device and is to be metered in; and/or a liquid-metering device which is designed to meter in a certain quantity of liquid depending on one or more process parameters and/or depending on a quantity of liquid which is determined by the control device and is to be metered in.

10. The device pursuant to claim 1, wherein:

at least one region of the conveyor section is arranged in an excrement-drying device; and/or different regions of the conveyor section are arranged in different excrement-drying devices.

11. The device pursuant to claim 1, wherein the excrement-introducing portion and the mixing portion are designed as an individual portion of the conveyor section.

12. The device pursuant to claim 1, wherein the conveyor section comprises two or more partial conveyor sections one above another, the partial conveyor sections having opposed conveyor directions and formed by a plurality of belt conveyors arranged one above another.

13. A system for residue use in livestock farming, comprising:

a device for residue use in livestock farming comprising a conveyor device for conveying animal excrement along a conveyor section, wherein the conveyor section has a larva-introducing portion for metering in larvae and/or larva eggs, an excrement-introducing portion for metering in animal excrement depending on one or more process parameters, a larva-separating portion for separating the larvae, a separating device comprising a light source and a larva bridge, the light source being adapted to illuminate the larva bridge, one or more first excrement-drying devices, and a second excrement-drying device, wherein:

regions of the conveyor section of the device for residue use are designed as drying belts of the one or more first excrement-drying devices and of the second excrement-drying device;

the larva-introducing portion is arranged in the first excrement-drying device;

the excrement-introducing portion is arranged between the first and the second excrement-drying device and/or between a plurality of first excrement-drying devices; and the larva-separating portion is arranged in the second excrement-drying device and/or is arranged downstream of the second excrement-drying device.

14. The system for residue use in livestock farming pursuant to claim 13, wherein the mixing portion is arranged between the first and the second excrement-drying device and/or between a plurality of first excrement-drying devices.

15. A method for residue use in livestock farming, comprising:

conveying animal excrement along a conveyor section, wherein the conveyor section has a larva-introducing portion, an excrement-introducing portion and a larva-separating portion, the larva-separating portion comprising a separating device with a light source and a larva bridge;

metering in larvae and/or larva eggs in the larva-introducing portion;

metering in animal excrement in the excrement-introducing portion depending on one or more process parameters;

separating the larvae in the larva-separating portion; and illuminating the larva bridge by the light source.

* * * * *